United States Patent [19]
McClelland

[11] 4,166,453
[45] Sep. 4, 1979

[54] BODY ELECTRODES

[75] Inventor: Brian McClelland, County Antrim, Northern Ireland

[73] Assignee: Cardio Technology Limited, Dublin, Northern Ireland

[21] Appl. No.: 870,251

[22] Filed: Jan. 17, 1978

[30] Foreign Application Priority Data

Jan. 21, 1977 [GB] United Kingdom ............... 2513/77

[51] Int. Cl.² .............................................. A61B 5/04
[52] U.S. Cl. ..................................... 128/639; 128/803
[58] Field of Search ............. 128/2.06 E, 2.1 E, 404, 128/410, 411, 416–418, DIG. 4

[56] References Cited

U.S. PATENT DOCUMENTS

| | | | |
|---|---|---|---|
| 3,496,929 | 2/1970 | Domingues | 128/2.06 E |
| 3,508,541 | 4/1970 | Westbrook et al. | 128/2.1 E |
| 3,534,727 | 10/1970 | Roman | 128/2.06 E |
| 3,542,010 | 11/1970 | Love | 128/2.1 E |
| 3,602,216 | 8/1971 | Moe, Jr. | 128/2.06 E |
| 3,659,614 | 5/1972 | Jankelson | 128/410 |
| 3,882,853 | 5/1975 | Gofman et al. | 128/2.06 E |
| 3,989,036 | 11/1976 | Sasamori | 128/2.06 E |
| 4,040,412 | 8/1977 | Sato | 128/2.1 E X |

*Primary Examiner*—Lee S. Cohen
*Attorney, Agent, or Firm*—Cushman, Darby & Cushman

[57] ABSTRACT

An electrode suitable for use in conducting electrical signals from the skin of a living animal, the electrode having a conducting member constituted by an electrically conducting plastics material and an electrically conducting chloride gel carried by a porous foam disc for contact with the skin, the porous foam disc being spaced from the conducting member by a non-electrically conducting element which is loaded with silver to provide electrical connection between the gel and the member.

5 Claims, 2 Drawing Figures

BODY ELECTRODES

This invention relates to an electrode that is suitable for use in conducting electrical signals from the skin of a living animal and to methods of assembling and operating the electrode.

Electrodes have previously been described that are suitable for this purpose and one embodiment of such an electrode is described in the specification of U.K. Pat. No 1,324,133 based on U.S. Ser. No. 11208 filed Feb. 13, 1970.

It is a requirement of these electrodes that they should be cheap to manufacture since they are disposable. It is also a requirement that, since the electrode is used to transmit signals having a very low power, they should be electrically stable during use. In use, the electrodes operate as a half cell employing an electrolyte which is commonly in the form of a gel.

The present invention enables an electrode to be provided which has a minimum number of parts and is simple and cheap to manufacture and which has improved electrical stability.

According to the invention there is provided an electrode which is suitable for use in conducting electrical signals from the skin of a living animal which includes a member to which electrical connection can be made, the member being made of an electrically conducting plastics material, an element carrying an electrically conducting gel so arranged that it can be positioned on the skin of an animal and a silver loaded element of non-electrically conducting material providing a physical barrier and an electrical connection between the gel and the member.

An embodiment of the invention will now be described, by way of example, with reference to the accompanying drawings in which.

Figure 1:
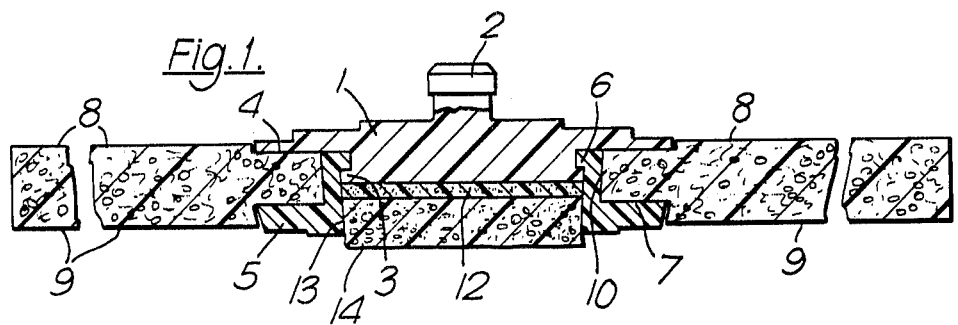
FIG. 1 is a vertical cross-section through an electrode.
Figure 2:
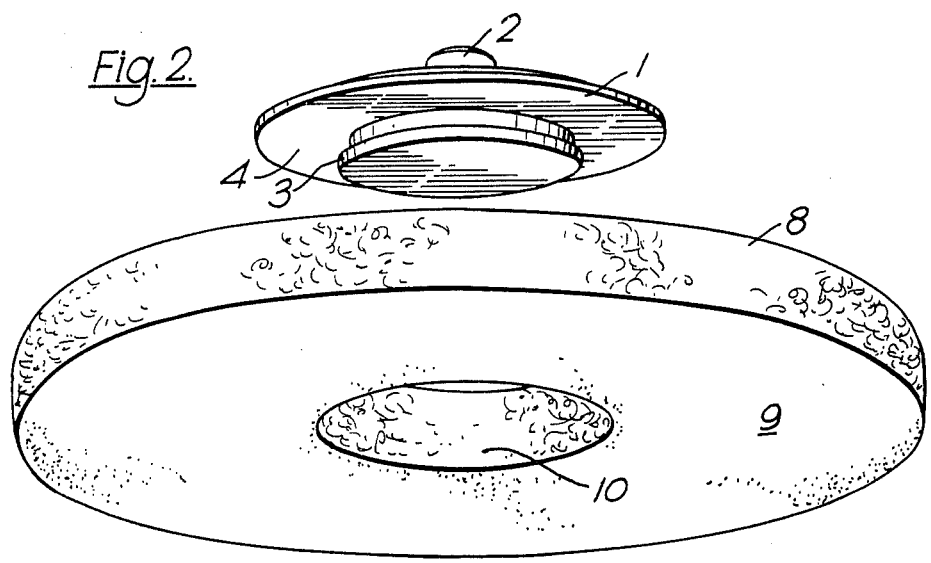
FIG. 2 is an exploded perspective view of the parts of the electrode shown in FIG. 1.

Referring to the drawings there is shown an electrode which includes a member 1 having a projecting ball-like connection portion 2 providing a mating connection with the socket of an electrical terminal. The member 1 which is made of an electrically conducting plastics material is moulded to shape.

Electrically conducting plastics material may, for example, be prepared by incorporating a good electrically conducting material, such as carbon, in powdered form into a polymeric binder material, for example an ethylene vinyl acetate co-polymer. A suitable conducting plastics material is known by the trade name Cabelec 887 and is available from Cabot Carbon Ltd., Bridge Street, Dukinfield, Cheshire, England.

The conducting plastics material can readily be formed to the shape shown to form a lip 3 spaced from a wide shoulder 4.

An annular member 5, made of a non-electrically-conducting plastics material, has an inner rim 6 and a wide shoulder 7. The rim 6 is so designed that, when the members 1 and 5 are assembled, the rim 6 snaps over the lip 3.

An elastic disc 8 of a foam plastics material having a backing of an adhesive material on its surface 9 and having a central hole 10 is positioned between the member 1 and the annular member 5 during assembly in such a way that it is gripped firmly between the shoulders 4 and 7.

A disc 12 of a non-electrically conducting fabric material which is loaded with silver dust is placed in a cavity 13, which is formed by the base of the member 1 and the inner wall of the annular member 5, against the base of the member 1.

Also within the cavity 13 there is pressed, on top of the disc 12, a disc 14 of a porous foam plastics material which is impregnated with an electrically conducting gel. The use of an electrically conducting gel held in a porous foam disc is well known and the gel employed in the preferred embodiment of the present invention is a chloride gel.

The disc 12 in the preferred embodiment of the invention is made of a non-woven fabric and a suitable material has been found to be a non-woven fabric grade 945 obtainable from Vilene Ltd., P.O. Box 3, Greetland, Halifax, West Yorkshire, England. This material has a stiffness and flexibility which enable it to be tumbled in the form of discs in silver dust so that it becomes loaded with silver dust, but is not mechanically damaged. The silver loaded disc 12 has the ability, in operation, to enable electrical contact to be made between the conducting gel held by the foam and the electrically conducting plastics member 1, while providing a barrier limiting the possibility of the gel from reaching the member 1 and developing an off-set potential. This arrangement enables an electrode to be provided which has a low ion-half-cell potential, thereby giving the low off-set potential characteristics and more stability than known electrodes The electrode is used in a well-known manner with the surface 9 of the disc 8 adhering to the skin of a subject and the gel carried by the disc 14 in electrical contact with the subject's skin. Electrical connection can be made to measuring apparatus via the connection portion 2.

During use, the interaction between ions of the gel and the silver, enables a comparatively stable silver-silver chloride junction to be produced.

It is possible to load silver in particle form on to other non-electrically conducting materials forming the disc 12. In experiments, for example, paper of a quality such as that used for kitchen cleaning rolls has been found to be suitable in used, although it is more difficult to load with silver than the preferred material.

It will be appreciated that although a particular embodiment has been described variations and modifications can be made within the scope of the appended claims.

I claim:

1. An electrode which is suitable for use in conducting electrical signals from the skin of a living animal, the said electrode including a member to which electrical connection can be made, the member being constituted by an electrically conducting plastics material, a first element carrying an electrically conducting gel, means for holding said first element to allow said first element to be positioned on the skin of an animal with the gel in electrical contact with the said skin and a silver loaded element of nonelectrically conducting material positioned between said first element and said member to provide a physical barrier between said member and first element to substantially prevent gel from reaching said member and an electrical connection via the silver loading between the gel and the member, whereby an electrical connection can be made between the skin and the member and the possibility of developing an off-set potential is reduced.

2. An electrode as claimed in claim 1 wherein said holding means includes a second annular member, the first mentioned and second members defining a cavity and the silver loaded element and the element carrying the gel being housed in the cavity.

3. An electrode as claimed in claim 1 wherein the electrically conducting plastics material is constituted by a carbon loaded ethylene vinyl acetate co-polymer.

4. An electrode as claimed in claim 1 wherein the silver loaded element is constituted by a non-woven fabric material.

5. An electrode as in claim 1, wherein said silver loaded element is substantially impervious to said gel.

* * * * *